United States Patent [19]
Jensen et al.

[11] Patent Number: 5,423,333
[45] Date of Patent: Jun. 13, 1995

[54] APPARATUS FOR SHOULDER IMMOBILIZATION

[75] Inventors: Nancy S. Jensen; Robert R. Moore, both of Hayward, Calif.

[73] Assignee: Orthopedic Systems, Inc., Hayward, Calif.

[21] Appl. No.: 200,411

[22] Filed: Feb. 23, 1994

[51] Int. Cl.6 .......................... A61F 5/37; A61F 5/00
[52] U.S. Cl. ............................ 128/878; 128/DIG. 20; 602/13
[58] Field of Search ................... 602/4, 5, 6, 13, 14, 602/19, 20, 21; 128/882, 882, 877, 878, 875DIG. 20

[56] References Cited

U.S. PATENT DOCUMENTS

| | | | |
|---|---|---|---|
| 607,666 | 7/1898 | Smith | 602/5 |
| 1,653,601 | 12/1927 | Foulke | 602/20 |
| 3,075,522 | 1/1963 | Cullen | 602/13 |
| 3,256,880 | 6/1966 | Caypinar | 128/877 |
| 3,762,405 | 10/1973 | DeGeorge | 602/13 |
| 3,786,805 | 1/1974 | Tourin | 602/13 |

FOREIGN PATENT DOCUMENTS 2589722  5/1987  France ................... 602/13
2589722  9/1991  France .

OTHER PUBLICATIONS

Promotional Literature for Dr. Arnaud Jolly's Shoulder Abductor (1986–1989).
B. Callens, J. Jaffrey, Appareillage postoperatoire d'apale (1987).

Primary Examiner—Michael A. Brown
Attorney, Agent, or Firm—Limbach & Limbach

[57] ABSTRACT

An apparatus for immobilizing a human shoulder, and for supporting the wrist of the arm associated with that shoulder, comprises three inflatable bladders joined together to form a triangular wedge. The wedge is positioned underneath the patient's arm such that one bladder is positioned along the patient's side, and such that the patient's arm rests on another of the bladders. The bladder that supports the patient's arm is provided with an inverted cup joined to an elongate step which supports the patient's hand and wrist.

10 Claims, 2 Drawing Sheets

APPARATUS FOR SHOULDER IMMOBILIZATION

FIELD OF THE INVENTION

The present invention relates to the field of devices for immobilizing limbs following orthopedic injuries or procedures. In particular, the present invention relates to the field of devices for effecting shoulder immobilization.

BACKGROUND OF THE INVENTION

It is often necessary for orthopedic specialists to secure the shoulders of patients against movement following injury or treatment of the shoulder. For example, shoulder immobilization is often required following trauma to the humeral head, rotator cuff, and brachial plexus. Moreover, procedures involving rotator cuff repair, shoulder arthroplasty, and other surgery of the shoulder necessitate post-surgical immobilization. Immobilization of the shoulder facilitates recovery and helps to prevent further injury during the recovery period.

For shoulder immobilization, it is normally preferable to maintain the upper arm in an abducted position, although the degree of abduction (i.e. the angle between the upper arm and the longitudinal axis of the body) depends upon the nature of the injury. Thus it is preferable for shoulder immobilization and abduction devices to be adjustable between varying degrees of abduction.

Various types of devices exist for effecting shoulder immobilization and abduction. One such device is comprised of three inflatable bladders sewn together to form a triangular wedge. A first side of the wedge is positioned along the side of the patient's torso and a second side of the wedge is positioned along the underside of the arm. Straps hold the wedge in place against the torso. During use, each of the bladders is inflated. For maximum abduction, the bladder forming the third side of the wedge is fully inflated such that the wedge forms a right triangle, with the third side forming the hypotenuse. If less than 90° abduction is desired, the third side of the triangle is deflated until the arm is in the desired position. A device of this type is disclosed in French Patent No. 2,589,722 which is hereinafter incorporated by reference.

While the above immobilization and abduction device is satisfactory for its intended purposes, it does not provide support for the wrist and hand. The patient's hand may therefore hang off of the wedge, possible causing discomfort, injury, or loss of circulation.

OBJECTS AND SUMMARY OF THE INVENTION

It is therefore an object of the present invention to provide a shoulder immobilization and abduction device that offers a selection of abduction positions. It is a further object of the present invention to provide a shoulder immobilization and abduction device that provides support to the wrist and hand without causing the device to be excessively cumbersome. It is yet another object of the present invention to provide a shoulder immobilization device having a wrist support which may moved between a selection of wrist positions without the use of heavy or cumbersome components. It will be shown that these objects and others will be achieved by the shoulder immobilizer of the present invention.

The shoulder immobilizer of the present invention is comprised of a plurality of bladders sewn together to form a substantially triangular wedge proportioned to be secured to the torso under the arm. A hand and wrist support member extends from the bladder which supports the arm.

DETAILED DESCRIPTION OF THE PREFERRED EMBODIMENT

The apparatus of the present invention is comprised generally of an inflatable wedge 10, straps 12A, 12B for securing the wedge to a patient's torso and a wrist support 14.

Figure 4:
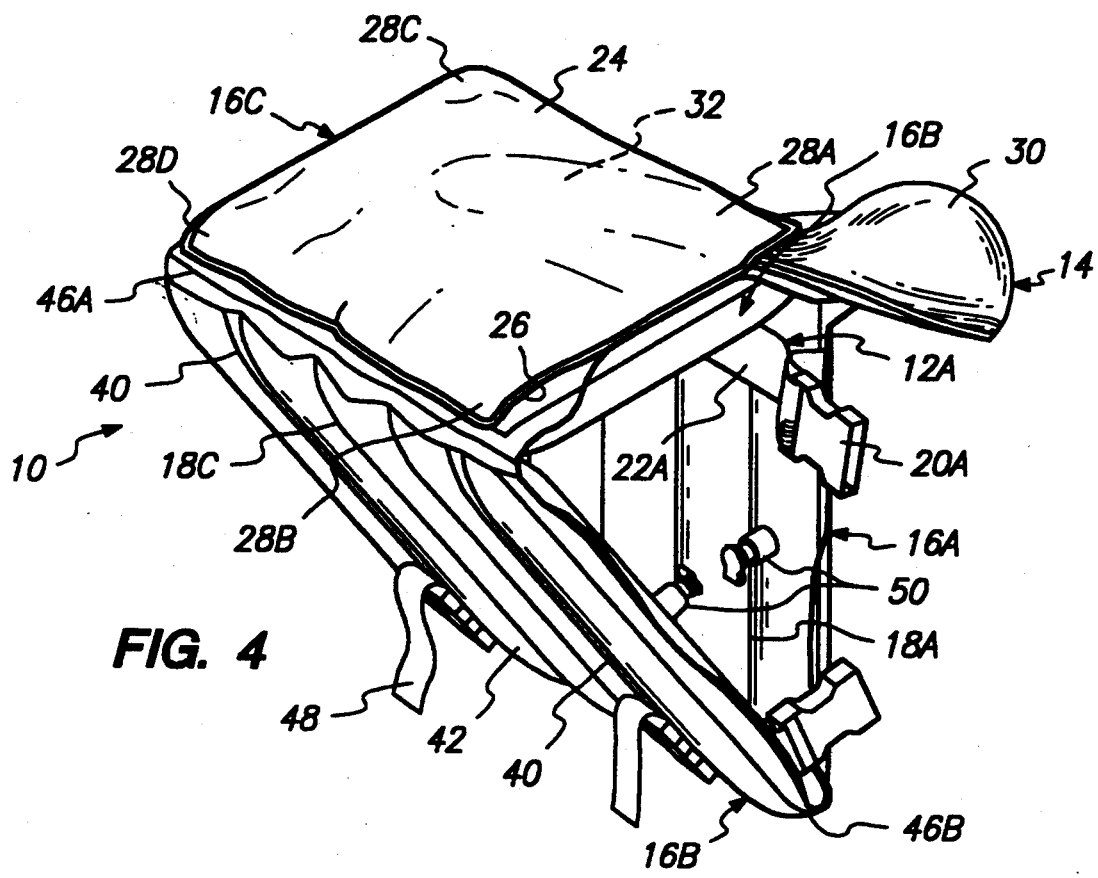
FIGS. 4 and 5 are perspective views of the shoulder immobilizer of the present invention, showing the wrist support device in alternate positions.
Figure 5:
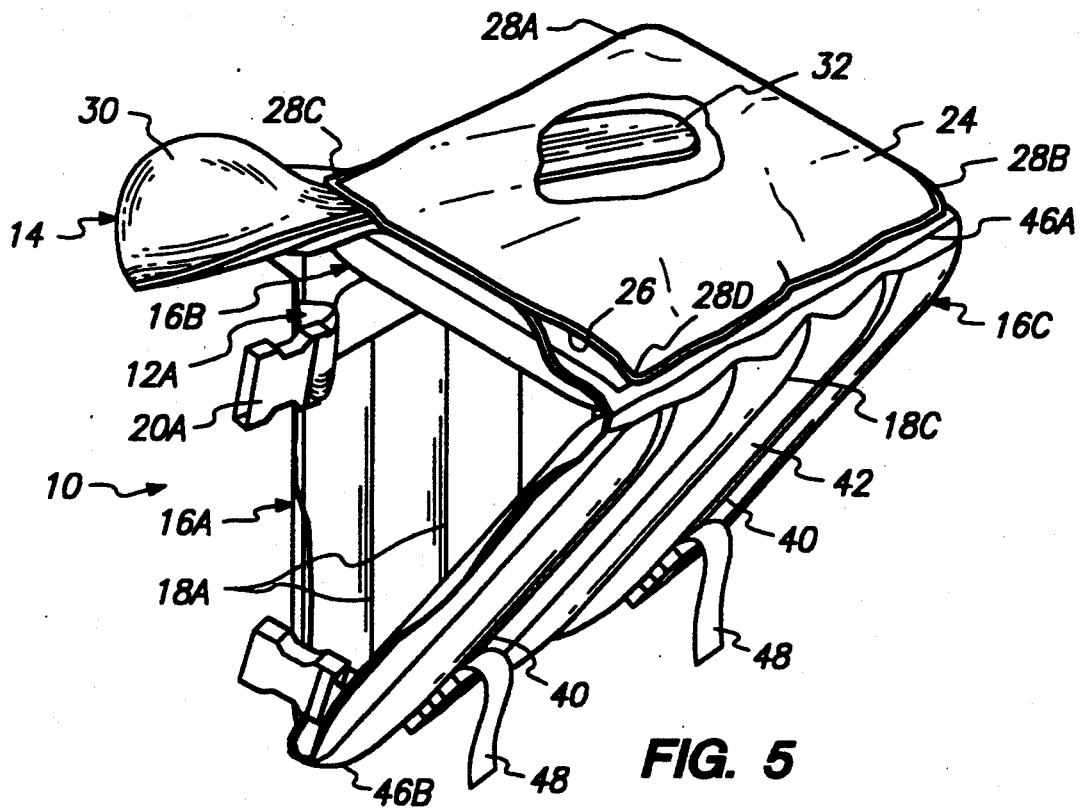

The wedge 10 is formed of three inflatable bladders 16A, 16B, 16C as shown in FIGS. 4 and 5. Each bladder 16A, 16B, 16C is formed of a two-ply nylon material having a plurality of spaced baffles, designated 18A, 18B and 18C, respectively, which are preferably formed by sewing the two layers of nylon together at the baffle locations.

Figure 1:
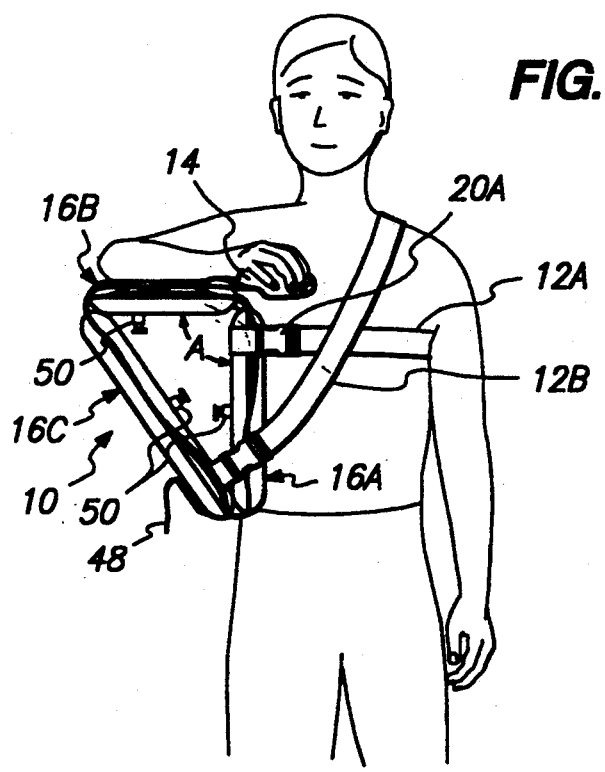
FIG. 1 is a front elevation view of the shoulder immobilizer of the present invention, schematically showing the invention as used to immobilize a person's shoulder.

First bladder 16A is provided with a first torso strap 12A which has a clasp 20A which is proportioned to extend around the torso of a patient and to couple with the clasp 20A, as shown in FIG. 1, to position first bladder 16A against the patient's side.

Second bladder 16B is connected to first bladder 16A such that the two bladders form a right angle between them when fully inflated. Second bladder has a top surface 24 which is covered with a layer 26 of fabric. The layer 26 is connected along its edges to the top surface 24, but it is unsecured to the top surface 24 at its corners, which are designated 28A through 28D. These unsecured corners of the layer 26 comprise sleeves through which access to the region between the second bladder 16b and the layer 26 may be obtained.

Figure 2:
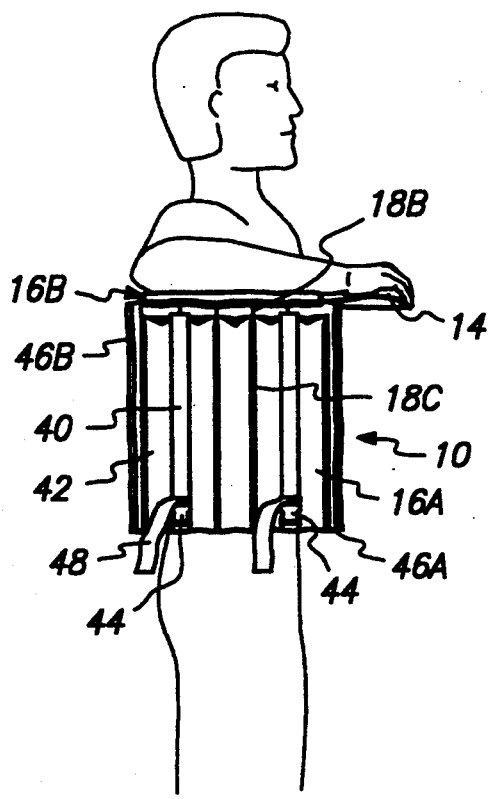
FIG. 2 is a side elevation view of the shoulder immobilizer of the present invention, schematically showing the invention as used to immobilize a person's shoulder.

Third bladder 16C is connected between the first and second bladders such that when the bladders are fully inflated the bladder 16C forms the hypotenuse of a right triangle formed by the three bladders. Connected to the lower portion of the third bladder is a shoulder strap 12B having a clasp 36 and proportioned to extend over the non-immobilized shoulder and to engage with the clasp 36. Abduction straps 40 extend along exterior face 42 of third bladder 16C, parallel to the baffles 18C, and are secured to the upper and lower edges 46A, 46B of the third bladder 16C as shown in FIG. 2. The abduction straps 40 pass through a pair of buckles 44 which allow the straps 40 to be tightened by pulling ends 48 of the straps 40 away from the buckles 44.

Figure 3:
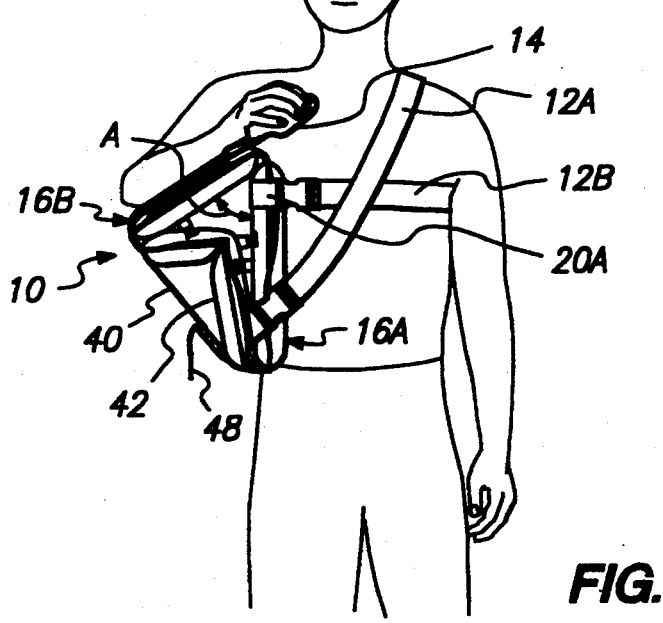
FIG. 3 is a front elevation view of the shoulder immobilizer of the present invention, schematically showing the invention as used to immobilize a person's shoulder using a smaller angle of abduction than that shown in FIG. 1.

Inflation valves 50 extending from each bladder provide ports through which air can be separately introduced into or released from each bladder. By releasing air from third bladder 16C and tightening the abduction straps 40, the angle of abduction, which is the angle formed between the first and second bladders 16A, 16B, can be decreased to less than 90° as shown in FIG. 3. By fully inflating each of the bladders, full 90° abduction may be carried out as shown in FIG. 1.

Referring to FIGS. 4 and 5, the wrist support 14 is comprised of a cup 30 and a rigid elongate stem 32 which is proportioned to be received within the sleeve formed between the fabric layer 26 on second bladder 16B at any of the corners 28A through 28D. Which corner the wrist support 14 is positioned at depends upon whether the patient's right or left arm is to be treated and further depends upon the angle at which the elbow is desired to be positioned. For example, in the configuration of FIG. 4, the wrist support 14 is positioned to support a patient's right wrist (such as is shown in FIG. 1) with the patient's elbow bent such that the forearm is angled towards the patient's body. If, in FIG. 4, the wrist support 14 was positioned within corner 28B rather than 28A, it would support the patient's right wrist with the patient's elbow at an angle of approximately 90°. Likewise, the wrist support 14 in FIG. 5 is positioned to support a patient's left wrist with the forearm angled towards the body. Moving the wrist support 14 from corner 28C to 28D would position it for supporting the patient's left wrist with the elbow at an approximate right angle.

In FIGS. 4 and 5 the wrist support 14 is positioned such that the entire length of the elongate stem 32 is positioned within the sleeve formed between the fabric layer 26 and the bladder 16B. However, the wrist support 14 may be extended further from the wedge such that a portion of the stem 32 protrudes out of the sleeve by a desired amount. This allows the immobilizer to be sized for use with patients of differing arm length.

To prevent the wrist support 14 from slipping out of place once it has been positioned between the bladder 16B and the fabric layer 26, the stem 32 is preferably covered by a material which is resistant to sliding against the fabric layer 26 due to its frictional properties relative to the fabric layer 26. In the preferred embodiment, the fabric layer 26 is comprised of a felt material and the stem 32 is covered by a porous plastic material which together help to secure the wrist support against sliding.

To use the device, the wrist support 14 is positioned in whichever of the corners (28A, 28B, 28C or 28D) will provide the desired wrist position. The wrist support 14 remains securely positioned between the bladder 16B and the fabric layer 26 due to the relative frictional properties of the fabric layer 26 and the porous plastic material covering the stem 32 of the wrist support 14.

An inflation medium, such as air, is next introduced into each bladder 16A, 16B, 16C via inflation ports 50 to fully inflate the bladders. Bladder 16B is positioned against the patients torso along the side of the patient corresponding to the shoulder sought to be immobilized. Straps 12A and 12B are positioned around the patient's torso and opposite shoulder, respectively, and are coupled to their respective buckles.

The arm corresponding to the shoulder being immobilized is next positioned such that the hand is cupped around the cup 30 of the wrist support 14 as shown in FIGS. 1 and 2. The abduction angle A may be decreased, as shown in FIG. 3, by releasing air from bladder 16C via its respective inflation port 50, and by pulling ends 48 of the abduction straps 40 to tighten the straps. Tightening the straps 40 compresses bladder 16C, causing it to fold as shown in FIG. 3, and thereby angles second bladder 16B in a downward direction.

We claim:

1. An apparatus for immobilizing a shoulder of a patient wherein the shoulder has an associated arm, wrist, and hand, the apparatus comprising:
    an inflatable thoracic bladder connectable to a thorax of the patient beneath the shoulder to be immobilized;
    an inflatable support bladder joined to the thoracic bladder at an angle, the inflatable support bladder having a support surface proportioned for supporting the arm;
    means for adjusting the angle between the thoracic bladder and the inflatable support bladder and for maintaining the angle at a desired degree; and
    support means for supporting the wrist and hand.

2. The apparatus of claim 1 wherein the support surface of the support bladder further comprises receiving means for receiving the support means and for securing the support means for supporting the wrist and hand in a desired position.

3. The apparatus of claim 2 wherein the receiving means is for selectively receiving the support means in one of a plurality of positions.

4. An apparatus for immobilizing a shoulder of a patient wherein the shoulder has an associated arm and wrist, comprising:
    an inflatable thoracic bladder connectable to a thorax of the patient beneath the shoulder to be immobilized;
    an inflatable support bladder joined to the thoracic bladder at an angle, the inflatable support bladder having a support surface proportioned for supporting the arm and further having a sleeve attached to the support surface;
    means for adjusting the angle between the thoracic bladder and the inflatable support bladder and for maintaining the angle at a desired degree; and
    an elongate stem having an end insertable into the sleeve and a cup secured to the end of the elongate stem.

5. The apparatus of claim 4 wherein the relative frictional properties of the elongate stem and the sleeve are sufficient to substantially secure the elongate stem within the sleeve by means of friction.

6. In an apparatus for immobilizing a human shoulder having an associated arm, wrist, and hand wherein the apparatus is of the type having an inflatable thoracic bladder connectable to a thorax of a patient beneath the shoulder to be immobilized, an inflatable support bladder joined to the thoracic bladder at an angle and having a support surface proportioned for supporting the arm, and a means for adjusting the angle between the thoracic bladder and the inflatable support bladder and for maintaining the angle at a desired degree, the improvement comprising:
    a hand support extending from the support surface.

7. In an apparatus for immobilizing a human shoulder having an associated arm and wrist wherein the apparatus is of the type having an inflatable thoracic bladder connectable to a thorax of a patient beneath the shoulder to be immobilized, an inflatable support bladder joined to the thoracic bladder at an angle and having a support surface proportioned for supporting the arm, and a means for adjusting the angle between the thoracic bladder and the inflatable support bladder and for maintaining the angle at a desired degree, the improvement comprising:

a wrist support extending from the support surface, the wrist support including an elongate stem having an end and a cup secured to the end of the elongate stem; and a sleeve attached to the support surface and proportioned for receiving the elongate stem.

8. The apparatus of claim 7 wherein the relative frictional properties of the elongate stem and the sleeve are sufficient to substantially secure the elongate stem within the sleeve by means of friction.

9. An apparatus for immobilizing a shoulder of a patient wherein the shoulder has an associated arm and wrist, comprising:

an inflatable thoracic bladder connectable to a thorax of the patient beneath the shoulder to be immobilized;

an inflatable support bladder joined to the thoracic bladder at an angle, the inflatable support bladder having a support surface proportioned for supporting the arm and further having a plurality of sleeves attached to the support surface;

means for adjusting the angle between the thoracic bladder and the inflatable support bladder and for maintaining the angle at a desired degree; and an elongate stem having an end selectively insertable into one of the sleeves and a cup secured to the end of the elongate stem.

10. In an apparatus for immobilizing a human shoulder having an associated arm and wrist wherein the apparatus is of the type having an inflatable thoracic bladder connectable to a thorax of a patient beneath the shoulder to be immobilized, an inflatable support bladder joined to the thoracic bladder at an angle and having a support surface proportioned for supporting the arm, and a means for adjusting the angle between the thoracic bladder and the inflatable support bladder and for maintaining the angle at a desired degree, the improvement comprising:

a wrist support having a stem extending from the support surface, the stem having means for supporting a patient's hand.

* * * * *

UNITED STATES PATENT AND TRADEMARK OFFICE
CERTIFICATE OF CORRECTION

PATENT NO. : 5,423,333
DATED : June 13, 1995
INVENTOR(S) : Nancy S. Jensen and Robert R. Moore It is certified that error appears in the above-indentified patent and that said Letters Patent is hereby corrected as shown below:

On the title page, item [57],
Abstract, Line 9, change "step" to --stem--

Column 1, Line 51, change "possible" to --possibly--

Column 1, Line 65, insert --be-- between "may" and "moved"

Column 2, Line 49, change "comers" to --corners--

Column 2, Line 50, change "comers" to --corners--

Column 3, Line 22, change "comer" to --corner--

Column 3, Line 27, change "comer" to --corner--

Column 3, Line 37, change "length" to --lengths--

Signed and Sealed this

Twenty-ninth Day of October 1996

Attest:

BRUCE LEHMAN

*Attesting Officer*  *Commissioner of Patents and Trademarks*